(12) United States Patent
Meurer et al.

(10) Patent No.: US 8,993,743 B2
(45) Date of Patent: Mar. 31, 2015

(54) CHIMERIC SURFACE ACTIVE PROTEINS

(75) Inventors: Guido Meurer, Seeheim-Jugenheim (DE); Esther Gabor, Zwingenberg (DE); Anke Bachert, Bickenbach (DE); Jürgen Eck, Bensheim (DE)

(73) Assignee: B.R.A.I.N. Biotechnology Research and Information Network AG, Zwingenberg (DE)

( * ) Notice: Subject to any disclaimer, the term of this patent is extended or adjusted under 35 U.S.C. 154(b) by 0 days.

(21) Appl. No.: 13/579,910

(22) PCT Filed: Feb. 18, 2011

(86) PCT No.: PCT/EP2011/052470
§ 371 (c)(1),
(2), (4) Date: Nov. 21, 2012

(87) PCT Pub. No.: WO2011/101457
PCT Pub. Date: Aug. 25, 2011

(65) Prior Publication Data
US 2013/0202697 A1    Aug. 8, 2013

(30) Foreign Application Priority Data

Feb. 18, 2010  (EP) ..................................... 10001681
Mar. 25, 2010  (EP) ..................................... 10003229

(51) Int. Cl.
*C07H 21/04*        (2006.01)
*C07K 14/37*        (2006.01)
(Continued)

(52) U.S. Cl.
CPC ................. *C07K 14/37* (2013.01); *C12N 15/62* (2013.01); *A61K 9/286* (2013.01);
(Continued)

(58) Field of Classification Search
None
See application file for complete search history.

(56) References Cited

U.S. PATENT DOCUMENTS 7,078,192 B2 *   7/2006  Linder et al. ................. 435/69.7
2005/0238685 A1 * 10/2005  Hektor et al. ................. 424/423
(Continued)

FOREIGN PATENT DOCUMENTS

| WO | 02/060877 A1 | 8/2002 |
|---|---|---|
| WO | 2007/139992 A2 | 12/2007 |
| WO | WO 2008110456 A2 * | 9/2008 |

OTHER PUBLICATIONS

GenBank Accession No. M32329.1, GI: 169868; Apr. 8, 1996.*
(Continued)

*Primary Examiner* — Rebecca Prouty
*Assistant Examiner* — Richard Ekstrom
(74) *Attorney, Agent, or Firm* — Roberts Mlotkowski Safran & Cole P.C.

(57) ABSTRACT

The present invention relates to a nucleic acid molecule encoding a chimeric protein having the biochemical activity of a surface active protein, wherein said chimeric protein comprises: (a) an N-terminal portion of a first surface active protein, wherein the N-terminal portion is devoid of between 0 and 10 of the most N-terminal amino acids of the mature first surface active protein; and, C-terminally thereof, (b) a C-terminal portion of a second surface active protein, wherein the C-terminal portion is devoid of between 0 and 10 of the most C-terminal amino acids of the mature second surface active protein. The present invention further relates to a vector, a non-human host and a method for the production of a chimeric protein having the biochemical activity of a surface active protein. In addition, the present invention relates to a chimeric protein encoded by the nucleic acid molecule of the invention and a composition comprising the chimeric protein. The chimeric protein may only consist of the above mentioned core of (a) and (b), but may also be flanked by additional components of the core, i.e. (a) or (b) or by (an) additional complete core(s) (a) and (b). The present invention furthermore relates to a method of coating and/or impregnating a material, comprising contacting the material with the chimeric protein or the composition of the invention.

15 Claims, 6 Drawing Sheets

Figure 1A:
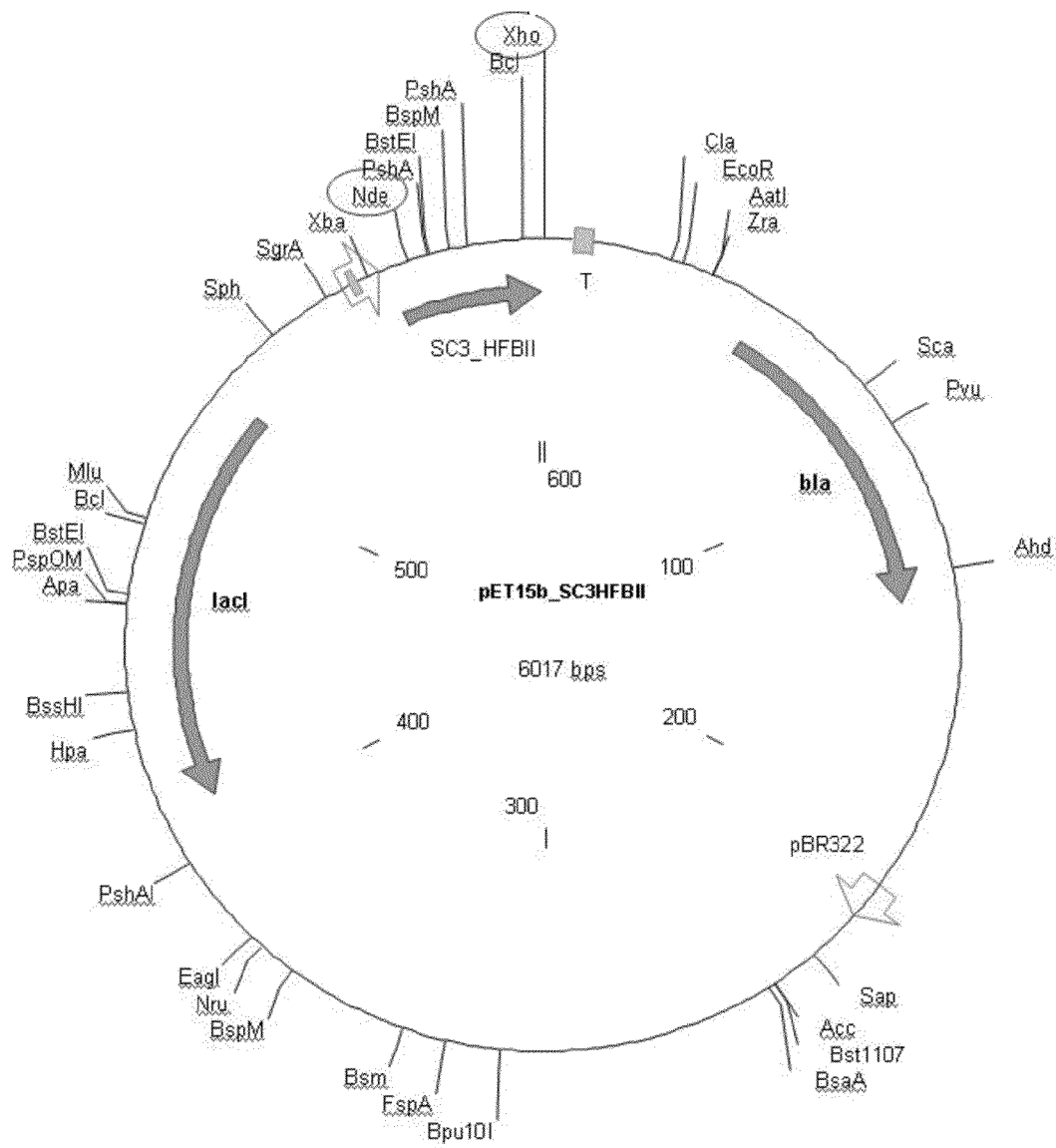

(51) Int. Cl.
*C12N 15/62* (2006.01)
*A61K 9/28* (2006.01)
*C09D 189/00* (2006.01)

(52) U.S. Cl.
CPC ............ *A61K 9/2873* (2013.01); *C09D 189/00* (2013.01)
USPC .................. 536/23.4; 536/23.74; 435/320.1; 435/252.3; 435/252.31; 435/252.32; 435/252.33; 435/252.34; 435/254.11; 435/254.2; 435/254.21; 435/254.23; 435/254.3; 435/325; 435/348; 435/419; 435/69.1; 435/69.7; 435/71.1; 435/71.2; 435/252.35

(56) References Cited

U.S. PATENT DOCUMENTS

| | | | | |
|---|---|---|---|---|
| 2009/0101167 | A1* | 4/2009 | Boeckh et al. | 134/6 |
| 2009/0136433 | A1* | 5/2009 | Subkowski et al. | 424/59 |
| 2009/0282729 | A1* | 11/2009 | Guzmann et al. | 44/301 |
| 2010/0170142 | A1* | 7/2010 | Posselt et al. | 44/301 |
| 2010/0330384 | A1* | 12/2010 | Gabor et al. | 428/537.5 |

OTHER PUBLICATIONS

GenBank Accession No. Y11894.1, GI: 1903324; Nov. 14, 2006.*
Scholtmeijer et al., "Surface modifications created by using engineered hydrophobins", Applied & Environmental Microbiology, vol. 68, No. 3, pp. 1367-1373, 2002.*
Lahtinen et al., "Hydrophobin (HFBI): a potential fusion partner for one-step purification of recombinant proteins from insect cells", Protein Expression & Purification, vol. 59, pp. 18-24, 2008.*
Linder et al., "Efficient purification of recombinant proteins using hydrophobins as tags in surfactant-based two-phase systems", Biochemistry, vol. 43, No. 37, pp. 11873-11882, 2004.*
Linder et al., "Surface adhesion of fusion proteins containing the hydrophobins HFBI and HFBII from *Trichoderma reesei*", Protein Science, vol. 22, pp. 2257-2266, 2002.*
Denner et al., Cloning of CYP11B1 and CYP11B2 From Normal Human Adrenal and Their Functional Expression in COS-7 and V79 Chinese Hamster Cells, Endocr. Res., 1995, 443-448, 21(1-2).
Ehmer et al., Development of a simple and rapid assay for the evaluation of inhibitors of human 17alpha-hydroxylase-C17,20-lyase (P450c17) by coexpression of P450c17 with NADPH-cytochrome-P450-reductase in *Escherichia coli*, J. Steroid Biochem. Mol. Biol., 2000, 57-63, 75(1).
Ehmer et al., Development of a test system for inhibitors of human aldosterone synthase (CYP11B2): screening in fission yeast and evaluation of selectivity in V79 cells, J. Steroid Biochem. Mol. Biol., 2002, 173-179, 81(2).
Hutschenreuter et al., Synthesis of Hydroxy Derivatives of Highly Potent Non-steroidal CYP 17 Inhibitors as Potential Metabolites and Evaluation of their Activity by a Non Cellular Assay using Recombinant Human Enzyme, J. Enz. Inhib. Med. Chem., 2004, 17-32, 19(1).
Jagusch et al., Synthesis, biological evaluation and molecular modelling studies of methyleneimidazole substituted biaryls as inhibitors of human 17alpha-hydroxylase-17,20-lyase (CYP17). Part I: Heterocyclic modifications of the core structure, Bioorg. Med. Chem., 2008, 1992-2010, 16(4).
Mornet et al., Characterization of Two Genes Encoding Human Steroid 11Beta-Hydroxylase(P-450 11Beta), J. Biol. Chem., 1989, 20961-20967, 264(35).
Roumen et al., Synthesis, Biological Evaluation, and Molecular Modeling of 1-Benzyl-1H-imidazoles as Selective Inhibitors of Aldosterone Synthase (CYP11B2), J. Med. Chem., 2010, 1712-1725, 53(4).
Swearingen et al. (Eds.), Contemporary Endocrinology: Diagnosis and management of Pituitary Disorders, 2008, Humana Press, Totowa, NJ (Table of Contents).
Thompson et al., Utilization of Oxygen and Reduced Nicotinamide Adenine Dinucleotide Phosphate by Human Placental Microsomes during Aromatization of Androstenedione, J. Biol. Chem., 1974, 5364-5372, 249(17).
Zolle et al., New Selective Inhibitors of Steroid 11Beta-Hydroxylation in the Adrenal Cortex. Synthesis and Structure-Activity Relationship of Potent Etomidate Analogues, J. Med. Chem., 2008, 2244-2253, 51(7).

* cited by examiner

```
  1 atgggcagca gccatcatca tcatcatcac agcagcggcc tggtgccgcg cggcagccat
    >>......His......>>
     h  h   h  h  h  h
                                                  >>......Trb.......>>
                                                   l  v  p  r  g  s 61 atgctgccag gcggccatcc tggcaccact acgcctcccg tcacgaccac ggtcaccgtc
    >>.............................SC3............................>
     l  p  g  g  h  p  g  t  t   t  p  p  v  t  t   t  v  t  v 121 accacccctc cgagcaccac caccatcgcc gccggaggca cctgcccgac aggattattc
    >.................SC3.................>>
     t  t  p  p  s  t  t  i  a  a  g  g   t
                                                  >>......HFBII......>
                                                   c  p  t  g  l  f 181 tcaaatccgc tttgctgcgc gacaaacgtc ctggatctta ttggcgtgga ctgtaaaacc
    >.............................HFBII...........................>
     s  n  p  l  c  c  a  t  n  v  l  d  l  i  g  v  d  c  k  t 241 ccgacgattg ctgtagatac gggcgcaatt tttcaagccc attgtgcaag taaggatct
    >.............................HFBII...........................>
     p  t  i  a  v  d  t  g  a  i  f  q  a  h  c  a  s  k  g  s 301 aaacctctttt gttgtgtcgc ccctgtggct gatcagacgt tattatgtca gaaagccatt
    >.............................HFBII...........................>
     k  p  l  c  c  v  a  p  v  a  d  q  t  l  l  c  q  k  a  i 361 ggcacattt ag
    >...HFBII..>>
     g  t  f  -
```

Figure 1B

```
               ....|....|  ....|....|  ...|....|  ....|....|  ....|....|
                       10          20         30          40          50
POH2.         --------GN  PKPTTTTVTV  TAPAHPTATA  PASECKTG--  -PVQCCNSVQ
POH3.         --------TN  P---------  ----------  PAPTCTTG--  -SLQCCNSVQ
SC3.          ---GGHPGTT  TPPVTTTVTV  TTPPSTTTIA  AGGTCTTG--  -SLSCCNQVQ
TT1.          LPNVGPSGKT  AHKPHQEPFW  PVQQDVTVEQ  AKAICGEGN-  -QVACCNEVS
HBFII.        ----------  ----------  ----------  --AVCPTGLF  SNPLCC----

SC3-HBFII     ---GGHPGTT  TPPVTTTVTV  TTPPSTTTIA  AGGTCPTGLF  SNPLCC----
SC3-POH3      ---GGHPGTT  TPPVTTTVTV  TTPPSTTTIA  AGGTCTTG--  -SLQCCNSVQ
SC3-TT1a      ---GGHPGTT  TPPVTTTVTV  TTPPSTTTIA  AGGTCGEGN-  -QVACCNEVS
SC3-TT1b      ---GGHPGTT  TPPVTTTVTV  TTPPSTTVEQ  AKAICGEGN-  -QVACCNEVS
                                            ⇧          ⇧
                                            fusion sites
```

Figure 1C

A

B

C

SEQUENCE LISTING

<160> NUMBER OF SEQ ID NOS: 4

<210> SEQ ID NO 1
<211> LENGTH: 309
<212> TYPE: DNA
<213> ORGANISM: Artificial sequence
<220> FEATURE:
<223> OTHER INFORMATION: /note="Description of artificial sequence: Fusion gene"

<400> SEQUENCE: 1

```
ctgccaggcg gccatcctgg caccactacg cctcccgtca cgaccacggt caccgtcacc    60
accccctccga gcaccaccac catcgccgcc ggaggcacct gcccgacagg attattctca   120
aatccgcttt gctgcgcgac aaacgtcctg gatcttattg gcgtggactg taaaaccccg   180
acgattgctg tagatacggg cgcaattttt caagcccatt gtgcaagtaa aggatctaaa   240
cctctttgtt gtgtcgcccc tgtggctgat cagacgttat tatgtcagaa agccattggc   300
acattttag                                                            309
```

<210> SEQ ID NO 2
<211> LENGTH: 102
<212> TYPE: PRT
<213> ORGANISM: Artificial sequence
<220> FEATURE:
<223> OTHER INFORMATION: /note="Description of artificial sequence: Fusion protein"

<400> SEQUENCE: 2

```
Leu Pro Gly Gly His Pro Gly Thr Thr Thr Pro Val Thr Thr Thr
 1               5                  10                  15

Val Thr Val Thr Thr Pro Pro Ser Thr Thr Thr Ile Ala Ala Gly Gly
             20                  25                  30

Thr Cys Pro Thr Gly Leu Phe Ser Asn Pro Leu Cys Cys Ala Thr Asn
         35                  40                  45

Val Leu Asp Leu Ile Gly Val Asp Cys Lys Thr Pro Thr Ile Ala Val
     50                  55                  60

Asp Thr Gly Ala Ile Phe Gln Ala His Cys Ala Ser Lys Gly Ser Lys
 65                  70                  75                  80

Pro Leu Cys Cys Val Ala Pro Val Ala Asp Gln Thr Leu Leu Cys Gln
                 85                  90                  95

Lys Ala Ile Gly Thr Phe
            100
```

<210> SEQ ID NO 3
<211> LENGTH: 372
<212> TYPE: DNA
<213> ORGANISM: Artificial sequence
<220> FEATURE:
<223> OTHER INFORMATION: /note="Description of artificial sequence: Fusion gene"

<400> SEQUENCE: 3

```
atgggcagca gccatcatca tcatcatcac agcagcggcc tggtgccgcg cggcagccat    60
atgctgccag gcggccatcc tggcaccact acgcctcccg tcacgaccac ggtcaccgtc   120
accacccctc cgagcaccac caccatcgcc gccggaggca cctgcccgac aggattattc   180
tcaaatccgc tttgctgcgc gacaaacgtc ctggatctta ttggcgtgga ctgtaaaacc   240
ccgacgattg ctgtagatac gggcgcaatt tttcaagccc attgtgcaag taaaggatct   300
aaacctcttt gttgtgtcgc ccctgtggct gatcagacgt tattatgtca gaaagccatt   360
```

-continued

```
ggcacatttt ag                                                    372

<210> SEQ ID NO 4
<211> LENGTH: 123
<212> TYPE: PRT
<213> ORGANISM: Artificial sequence
<220> FEATURE:
<223> OTHER INFORMATION: /note="Description of artificial sequence:
      Fusion protein"

<400> SEQUENCE: 4

Met Gly Ser Ser His His His His His His Ser Ser Gly Leu Val Pro
1               5                   10                  15

Arg Gly Ser His Met Leu Pro Gly Gly His Pro Gly Thr Thr Thr Pro
                20                  25                  30

Pro Val Thr Thr Thr Val Thr Val Thr Thr Pro Pro Ser Thr Thr Thr
                35                  40                  45

Ile Ala Ala Gly Gly Thr Cys Pro Thr Gly Leu Phe Ser Asn Pro Leu
        50                  55                  60

Cys Cys Ala Thr Asn Val Leu Asp Leu Ile Gly Val Asp Cys Lys Thr
65                  70                  75                  80

Pro Thr Ile Ala Val Asp Thr Gly Ala Ile Phe Gln Ala His Cys Ala
                85                  90                  95

Ser Lys Gly Ser Lys Pro Leu Cys Cys Val Ala Pro Val Ala Asp Gln
                100                 105                 110

Thr Leu Leu Cys Gln Lys Ala Ile Gly Thr Phe
            115                 120
```

CHIMERIC SURFACE ACTIVE PROTEINS

The present invention relates to a nucleic acid molecule encoding a chimeric protein having the biochemical activity of a surface active protein, wherein said chimeric protein comprises: (a) an N-terminal portion of a first surface active protein, wherein the N-terminal portion is devoid of between 0 and 10 of the most N-terminal amino acids of the mature first surface active protein; and, C-terminally thereof, (b) a C-terminal portion of a second surface active protein, wherein the C-terminal portion is devoid of between 0 and 10 of the most C-terminal amino acids of the mature second surface active protein. The present invention further relates to a vector, a non-human host and a method for the production of a chimeric protein having the biochemical activity of a surface active protein. In addition, the present invention relates to a chimeric protein encoded by the nucleic acid molecule of the invention and a composition comprising the chimeric protein. The chimeric protein may only consist of the above mentioned core of (a) and (b), but may also be flanked by additional components of the core, i.e. (a) or (b) or by (an) additional complete core(s) (a) and (b). The present invention furthermore relates to a method of coating and/or impregnating a material, comprising contacting the material with the chimeric protein or the composition of the invention.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Surface active agents change the chemical and physical properties of an interface when adsorbed onto the surfaces of dispersed particles. Amphiphilic surface active agents, for example, consist of hydrophobic and hydrophilic segments. The hydrophobic segment adsorbs onto non-polar surfaces or is attracted to a non-polar phase whereas the hydrophilic segment adsorbs onto a polar surface or is attracted to a polar phase. Surface active agents can thus be employed to render hydrophilic surfaces hydrophobic and hydrophobic surfaces hydrophilic. Certain surface active agents can self-assemble at any hydrophilic-hydrophobic interface into an amphipathic film. Such a self-assembly can significantly improve the properties of (bio)polymers. At solid/water interfaces, surface active agents reduce the water surface tension which results in a change of the contact angle of a water-droplet. This parameter can be used for the measurement of the activity of a surface active agent.

Some proteins of natural origin act as surface active agents. These include for example latherin from horse sweat (see e.g. J. G. Bealey et al., Biochem J. 1986 May 1; 235(3): 645-650), phospholipase C, amyloid or amyloid-like proteins, such as amyloid-β,β-casein, the bio-emulsifier of *Acinetobacter radioresistens* KA53 referred to as alasan, HCf-1 from *Cladiosporum fulvum* (see e.g. Spanu, P., Gene 1997, 193: 89-96), SapB from *S. coelicolor* A3(2) and *S. tendae*, glyko-lipid transfer protein, curlines (see e.g. M. R. Chapman et al, Science 2002, 295 (5556): 851-855; M. M. Barnhart and M. R. Chapman, Annu Rev Microbiol. 2006, 60:131-47), chaplins (see e.g. Elliot et al., Genes Dev. 2003, 17: 1727-1740) and rodlins (see e.g. D. Claessen, Mol. Microbiol. 2004, 53(2): 433-443) or proteins from the family commonly referred to as hydrophobins (see e.g. Minireview by Scholtmeijer, K. et al., Appl. Microbiol. Biotechnol. (2001) 56: 1-8).

The use of an engineered class I hydrophobin (SC3) to achieve surface modifications, i.e. altered wettability and enhanced growth of fibroblasts, has been described by Scholtmeijer, K. et al. (Surface modifications created by using engineered hydrophobins, Appl. Environ. Microbiol. 2002, 68(3): 1367-73).

The patent application WO 2006/082251A2 discloses a genetic engineering method of preparing hydrophobins that do not occur naturally. Similarly, WO 2006/082253A2 describes the use of hydrophobin fusion proteins for the coating of surfaces.

Apart from changing biophysical properties of surfaces, hydrophobins can further be used to attach molecules (e.g. enzyme, antibody, nucleic acid) to surfaces for which they normally lack a high affinity (WO 2004/000880 A1).

The utilization of these properties of surface active proteins, and in particular hydrophobins, includes applications such as coatings, emulsion stabilization and separation technologies. For example, surfaces such as e.g. Teflon® can be coated to obtain a hydrophilic surface; surfaces of implants can be modified or silicon surfaces can be protected in e.g. etch processes.

The coating of surfaces has been described at elevated temperatures (EP 1252516 B1) as well as at low temperatures (e.g. around room temperature) when suitable conditions are applied, such as for example the presence of a detergent, control of the pH of the coating solution or increasing the concentration of the surface active protein, e.g. a hydrophobin (US 2007/0166346).

EP 1254158 B1 describes a general method for coating a surface with hydrophobin.

WO 96/41882 proposes the use of hydrophobins as emulsifiers, thickeners or surface-active substances for rendering hydrophobic surfaces hydrophilic, for improving the water resistance of hydrophilic substrates and for preparing oil-in-water or water-in-oil emulsions.

EP 1252516B1 describes a method of treating the surface of objects like glass, contact lenses or medical devices with a hydrophobin-containing solution.

The use of hydrophobins as a component of cleansing agents for hard surface soil-repellent treatment is described in WO 2006/103215A1.

US 2003/0217419 A1 proposes pharmaceutical uses, such as the preparation of ointments or creams, and cosmetic uses, such as skin protection or the preparation of hair shampoos or hair conditioners.

Cosmetic uses are further proposed in WO 2006/136607 and US 2009/0136433 A1, where the binding properties of hydrophobins to keratin, mucosa or teeth are utilized to direct cosmetic effector molecules, e.g. in the form of compositions or conjugates with a hydrophobin, to the desired site of action (hair, nails, skin).

Furthermore, WO 2009/037061 proposes hydrophobin polypeptides as penetration enhancers in pharmaceutical and cosmetic compositions.

In addition, fusion proteins comprising class I hydrophobins were described for different applications. WO 2006/131564 A3R4 and WO 2006/082251 A2 disclose cysteine-depleted hydrophobin fusion proteins of class I hydrophobins and bacterial proteins. In WO 2006/103252 A2, the use of hydrophobin fusion proteins of class I hydrophobins and bacterial proteins as phase stabilizers is proposed, whereas WO 2006/103253 A2 describes the use of such fusion proteins in drilling fluid.

None of the prior art documents describes chimeric surface active proteins comprising a combination of protein portions derived from different surface active proteins. Despite the above described advances in the development of surface active proteins, there is still the need to provide improved surface active proteins.

This need is addressed by the provision of the embodiments characterized in the claims.

Accordingly, the present invention relates in a first embodiment to a nucleic acid molecule encoding a chimeric protein having the biochemical activity of a surface active protein, wherein said chimeric protein comprises: (a) an N-terminal portion of a first surface active protein, wherein the N-terminal portion is devoid of between 0 and 10 of the most N-terminal amino acids of the mature first surface active protein; and, C-terminally thereof, (b) a C-terminal portion of a second surface active protein, wherein the C-terminal portion is devoid of between 0 and 10 of the most C-terminal amino acids of the mature second surface active protein.

In accordance with the present invention the term "nucleic acid molecule" defines a linear molecular chain consisting of more than 30 nucleotides. The group of molecules designated herein as "nucleic acid molecules" also comprises complete genes. The term "nucleic acid molecule" is interchangeably used herein with the term "polynucleotide".

The term "nucleic acid molecules", in accordance with the present invention, includes DNA, such as for example cDNA or genomic DNA, and RNA. It is understood that the term "RNA" as used herein comprises all forms of RNA including mRNA. Preferably the term "nucleic acid molecule" refers to genomic DNA, cDNA or mRNA. In a more preferred embodiment the nucleic acid molecule is DNA. The nucleic acid sequence may also comprise regulatory regions or other untranslated regions. Further included are nucleic acid mimicking molecules known in the art such as for example synthetic or semi-synthetic derivatives of DNA or RNA and mixed polymers, both sense and antisense strands. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon. They may contain additional non-natural or derivative nucleotide bases, as will be readily appreciated by those skilled in the art.

The present invention furthermore contemplates nucleic acid molecules complementary to the above-defined nucleic acid molecule as well as nucleic acid molecules hybridizing thereto under stringent conditions.

It is well known in the art how to perform hybridization experiments with nucleic acid molecules. Correspondingly, the person skilled in the art knows what hybridization conditions he/she has to use to allow for successful hybridization. The establishment of suitable hybridization conditions is referred to in standard text books such as Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985).

"Stringent conditions" refer to hybridization conditions which allow nucleic acid molecules capable of hybridizing to the nucleic acid molecules of the invention or parts thereof to hybridize to these target sequences to a detectably greater degree than to other sequences (e.g. at least 2-fold over background). Stringent conditions are sequence-dependent and will differ depending on the circumstances. By controlling the stringency of the hybridization and/or washing conditions, target sequences that have at least 90% sequence identity, more preferably 95%, such as 98% and more preferably 100% sequence identity to the respective probe, i.e. the nucleic acid molecule of the invention, can be identified (highly stringent hybridization conditions). Alternatively, stringency conditions can be adjusted to allow a higher degree of mismatching in sequences (low stringency conditions of hybridization). Such highly stringent and low stringent conditions for hybridization are well known to the person skilled in the art. The embodiment recited herein above preferably refers to highly stringent conditions. For example, highly stringent conditions for hybridization comprise e.g. an overnight incubation at 65° C. in 4×SSC (600 mM NaCl, 60 mM sodium citrate) followed by washing at 65° C. in 0.1×SSC for one hour. Alternatively, highly stringent hybridization conditions can comprise an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulphate, and 20 µg/ml denatured, sheared salmon sperm DNA, followed by washing in e.g. 0.1-0.5×SSC at about 55-65° C. for about 5 to 20 min. Changes in the stringency of hybridization are primarily accomplished through the manipulation of formamide concentration (lower percentages of formamide result in lowered stringency), salt conditions, or temperature, as is well known to the skilled person.

The term "protein" as used herein describes a group of molecules consisting of one or more linear chains of more than 30 amino acids selected from the 20 amino acids of the genetic code, joined by peptide bonds. Proteins may further form dimers, trimers and higher oligomers, i.e. consisting of more than one molecule which may be identical or non-identical. The corresponding higher order structures are, consequently, termed homo- or heterodimers, homo- or heterotrimers etc. The term "protein" (wherein "protein" is interchangeably used herein with "polypeptide") also refers to naturally modified peptides/proteins wherein the modification is effected e.g. by glycosylation, acetylation, phosphorylation and the like. Such modifications are well-known in the art.

In accordance with the present invention, the term "chimeric protein having the biochemical activity of a surface active protein" refers to a chimeric protein capable of changing the chemical and physical properties of an interface when adsorbed onto a surface. In particular, the chimeric protein having the biochemical activity of a surface active protein is preferably a protein with amphiphilic properties, particularly a protein that is capable of forming layers on hydrophobic or hydrophilic surfaces. Preferably, the chimera of the invention thus possesses at least one of the capability to achieve surface modifications, e.g. altered wettability or confers prolonged stability of tablets. Methods to test for these biological activities of surface active proteins are well known to the skilled person and include, without being limiting, the methods described in the appended examples. Thus, objects can for example be brought into contact with the chimeric surface active protein of the invention or with a native surface active protein and surface tensiometry or measurement of contact angles obtained with water droplets, may be performed as described by Martin, G. G. et al., Biomacromolecules 2000, 1, 49-60, and Yoo, D. et al., Macromolecules 1998, 31, 4309-4318.

In accordance with the present invention, the term "chimeric protein having a biochemical activity of a surface active protein" is interchangeably used with "chimera of the invention", "chimeric protein of the invention" or "chimeric surface active protein of the invention".

The term "chimeric", as used herein, refers to the fact that the surface active protein has an amino acid sequence derived from at least two different surface active proteins, wherein neither of these proteins is present as the naturally occurring full-length protein. Thus, the chimeric surface active protein of the invention comprises an N-terminal portion derived from a first surface active protein, which is devoid of between 0 and 10 of the most N-terminal amino acids of the mature first surface active protein, while the C-terminal portion is derived from a second surface active protein, which is devoid of between 0 and 10 of the most N-terminal amino acids of the mature second surface active protein. In this regard, it is preferred with increasing preference that the N-terminal portion and/or the C-terminal portion is devoid of between 0 and 9, between 0 and 8, between 0 and 7, between 0 and 6, between 0 and 5, between 0 and 4, between 0 and 3, between 0 and 2, or 0 and/or 1 of the most N-terminal or the most C-terminal amino acids, respectively. It is most preferred that the N-terminal portion includes the most N-terminal amino acid of the mature first surface active protein and/or the C-terminal portion includes the most C-terminal amino acid of the mature second surface active protein. The second surface active protein may be chosen from the same or a different group of proteins or subclasses of proteins, as long as the protein is not identical to the first surface active protein.

Accordingly, in a preferred embodiment of the nucleic acid molecule of the invention, the N-terminal portion includes the most N-terminal amino acid of the mature first surface active protein, and the C-terminal portion includes the most C-terminal amino acid of the mature second surface active protein.

The invention furthermore relates to a nucleic acid molecule encoding a chimeric protein having the biochemical activity of a surface active protein, wherein said chimeric protein comprises (a) an N-terminal portion of a class I hydrophobin including the most N-terminal amino acid thereof; and, C-terminally thereof, (b) a C-terminal portion of a class II hydrophobin including the most C-terminal amino acid thereof.

It is moreover preferred that the N-terminal portion of the chimeric surface active protein consists of at least 3%, such as at least 10%, such as at least 20% such as for example at least 30% or such as more than 30% of the N-terminal amino acid sequence of the first surface active protein. Also envisaged herein is that the N-terminal portion of the chimeric surface active protein consists of at least 40%, such as for example at least 50%, such as at least 60% such as for example at least 70% or such as more than 80% of the N-terminal amino acid sequence of the first surface active protein. Further envisaged is that the N-terminal portion of the chimeric surface active protein consists of at least 90%, such as for example at least 95%, such as at least 97% or such as of 99% of the N-terminal amino acid sequence of the first surface active protein. The percentages indicated above refer to percentages of the of the N-terminal amino acid sequence of the first surface active protein starting from (into the direction of the C-terminus) and including the most N-terminal amino acid of the mature protein. The invention, however, also comprises embodiments where the most N-terminal amino acid(s) such as the one, two, three, four, five, six, seven, eight, nine or ten most N-terminally located amino acids have been deleted.

The term "comprises" includes the meaning of the term "consists of".

The term "N-terminal amino acid sequence of the first surface active protein" as used herein refers to an amino acid sequence starting from the most N-terminal amino acid of the mature first surface active protein, wherein said amino acid sequence is devoid of between 0 and 10 of the most N-terminal amino acids of the mature amino acid sequence and excluding at least the most C-terminal amino acid of the mature amino acid sequence. Thus, in case the amino acid sequence is devoid of 0 of the most N-terminal amino acids of the mature amino acid sequence it refers to an amino acid sequence starting from and including the most N-terminal amino acid of the mature first surface active protein and excluding at least the most C-terminal amino acid of the mature amino acid sequence.

In such cases where the amino acid sequence is devoid of 1, 2, 3, 4, 5, 6, 7, 8, 9 or 10 of the most N-terminal amino acids of the mature amino acid sequence, the N-terminal portion starts with the second, third, fourth, fifth, sixth, seventh, eighth, ninth, tenth or eleventh amino acid counted from the N-terminus of the mature protein, respectively. It is also envisaged in different embodiments that the chimeric protein comprises N-terminally of the N-terminal protein of the mature first surface active protein further heterologous amino acids such as a amino acids forming a tag and/or amino acids forming a protease cleavage site. It is also envisaged that said further amino acids confer a biochemical activity such as an enzymatic activity. It is further preferred that the at least 3% of the amino acid sequence (or the percentage of the amino acid sequence of any one of the preferred or alternative embodiments) corresponds to a consecutive stretch of amino acids also found in the protein, preferably a naturally occurring protein, from which the N-terminal portion is derived. Yet, the invention also comprises embodiments where amino acids from said stretch of amino acids found in the protein from which the N-terminal portion has been derived have been deleted, substituted for different amino acids, preferably with similar properties, or embodiments where amino acids have been inserted, duplicated or where stretches of amino acids have been inverted. All these manipulations to the N-terminal portion can be effected by the skilled person and the resulting N-terminal portion, in the context of the chimeric protein of the invention, tested for the properties described herein for said chimeric protein. It is understood that the chimeric protein of the invention maintains these properties or essentially (>80% of the above recited biochemical activity) maintains these properties. Appropriate tests for determining (essential) maintenance of the biological function of the protein are known in the art or described in this specification.

The term "C-terminal amino acid sequence of the second surface active protein" as used herein refers to an amino acid sequence starting from the most C-terminal amino acid of the mature second surface active protein, wherein said amino acid sequence is further devoid of between 0 and 10 of the most C-terminal amino acids of the mature amino acid sequence and excluding at least the most N-terminal amino acid of the mature amino acid sequence. Thus, in case the amino acid sequence is devoid of 0 of the most C-terminal amino acids of the mature amino acid sequence it refers to an amino acid sequence starting from and including the most C-terminal amino acid of the mature first surface active protein and excluding at least the most N-terminal amino acid of the mature amino acid sequence.

The C-terminal portion of the chimeric surface active protein consists of at least 3%, preferably at least 10%, more preferably at least 20% such as for example at least 30%, more preferably at least 40%, even more preferred at least 50%, such as for example at least 60%, such as for example at least 70%, more preferably at least 80%, such as for example at least 90%, more preferably at least 95%, even more preferably of at least 97% and most preferably of 99% of the amino acid sequence of the second surface active protein, starting from (in the direction of the N-terminus) and including the most C-terminal amino acid of the mature protein. The various definitions, alternative and preferred embodiments provided in connection with the N-terminal portion herein above apply mutatis mutandis to the C-terminal portion, with the exception that "N-terminus/N-terminal portion" has to be replaced by "C-terminus/C-terminal portion".

Preferably, the overall length of the chimeric surface active protein is maintained in the range observed for the naturally occurring surface active proteins from which the chimeric surface active protein is derived. That range is defined by the length of the individual surface active proteins used, i.e. for the surface active proteins used in the examples below, the first surface active protein has a length of 112 amino acids while the second surface active protein has a length of 71 amino acids. The range for the overall length of a chimeric surface active protein as represented in the examples thus is preferably between 71 and 112 amino acids.

As is evident from the above, the percentage values of the N-terminal portion and of the C-terminal portion as a rule do not add up to 100%, implying that the chimeric protein will usually differ in the overall number of amino acids from the overall number of amino acids of the first and second surface active protein.

Further envisaged is that where a certain percentage, such as for example 70%, of the amino acid sequence of the second surface active protein starting from the C-terminus is included in the chimeric surface active protein, the overall number of amino acids in the chimeric protein equals that of the second surface active protein (similar constructs are envisaged in which the overall number of amino acids of the chimeric protein equals that of the first surface active protein). In other terms, the remaining amino acids of the full length chimeric protein, in this example amounting to 30% of the overall amino acid sequence of the second surface active protein, are provided by the first surface active protein starting from and including the most N-terminal amino acid of the mature second surface active protein. As is evident from the above, the invention is not confined to such exemplary embodiments. In the above mentioned example, the N-terminal portion derived from the first surface active protein may amount to e.g. 25% or 35% of the overall amino acid sequence of the second surface active protein. Furthermore, the invention allows for the inclusion of amino acid sequences not derived from either the first nor the second surface active protein. For example, such heterologous sequence may form a linker between those portions or a tag (see below).

Most preferably, more than 31% of the amino acid sequence of the chimeric surface active protein consist of the N-terminal amino acid sequence of the first surface active protein. It is again understood that the percentage preferably refers to consecutive amino acids and is relative to the overall length of the chimeric surface active protein. Alternative or preferred embodiments as referred to above apply here mutatis mutandis as well.

The terms "the amino acid sequence of a first surface active protein" and "the amino acid sequence of a second surface active protein" refer to amino acid sequences of both naturally occurring surface active proteins as well as amino acid sequence derived there from, for example by mutation etc., as explained above.

The nucleic acid molecule of the invention encoding the chimeric surface active protein may be obtained by joining of a polynucleotide encoding the respective portion of the amino acid sequence of a first surface active protein with another polynucleotide encoding the respective portion of the amino acid sequence of a second surface active protein. Translation of the fused polynucleotide of the invention results in the expression of the chimeric surface active protein of the invention as a single-chain protein. It is preferred that the thus expressed chimeric protein is a soluble protein and/or secreted from the host cell in which it is expressed.

Preferably, the nucleic acid molecule of the invention further comprises a purification tag, i.e. a sequence for facilitating the purification of the recombinant chimeric protein after expression in a host, such as for example E. coli. Suitable sequences for facilitating purification include, without being limiting are His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein, with 6×His being preferred for the molecule of the present invention. The suitable sequence for facilitating purification is preferably a His or GST and even more preferred a His (e.g. a 6×His). Generally, such purification tags are fused to the N-terminus of the coding sequence of the chimeric surface active protein.

It is further preferred that a protease cleavage site is comprised in the nucleic acid molecule of the invention which is preferably located between the purification tag and the coding sequence for the chimeric surface active protein to allow for the removal of the tag sequence after purification. Protease cleavage sites are well known to the skilled person and include, without being limiting, a specific site for cleavage by thrombin, factor Xa, TEV (tobacco etch virus protease), clostripain, caspase, enterokinase, pepsin, thermolysin, proteinase K or granzyme B. Preferably, the specific site for cleavage is a specific site for cleavage by thrombin (i.e. a thrombin site).

Alternatively, chemical cleavage sites like CNBr, NTCB, iodosobenzoic acid, hydroxylamine and other well known chemical cleavage sites can be utilized for the removal of the tag sequence.

Further envisaged are chimeric surface proteins that comprise a multiple of the core, i.e. [(a) an N-terminal portion of a first surface active protein, wherein the N-terminal portion is devoid of between 0 and 10 of the most N-terminal amino acids of the mature first surface active protein; and, C-terminally thereof, (b) a C-terminal portion of a second surface active protein, wherein the C-terminal portion is devoid of between 0 and 10 of the most C-terminal amino acids of the mature second surface active protein]. A multiple, in accordance with the present invention means 2 or more, such as 3 or 4. Preferably, the upper limit of the core is 2. Also envisaged is that the core or the multiple of the core is flanked by individual members (a) or (b) wherein (a) is adjacent to (b) (but not to (a)) and (b) is adjacent to (a) (but not to (b)). Whereas the applicant does not wish to be bound by any theory, such constructs could provide advantages in terms of expression yields. For example, if (b) alone is difficult to express, flanking (b) on both sides with (a) may improve expression of (b).

In accordance with the present invention it was found that the generation of a chimeric protein of the invention confers surprising and advantageous properties to the resulting protein. More specifically, the invention surprisingly enabled the recombinant expression of a class II hydrophobin (HFBII), which is a surface active protein which was previously not expressible, recombinantly. As is shown in the examples, the N-terminal sequence of HFB II was replaced by the N-terminal amino acids of a class I hydrophobin (SC3). Whereas any attempt to express the native hfb2 gene in E. coli failed, the fusion of a small N-terminal fragment of SC3 to a portion of HFB II that lacks the corresponding N-terminus yielded considerable expression of the recombinant fusion protein in *E. coli* and, after chromatographic purification, a chimeric protein of high purity possessing new properties.

After recombinant expression of the chimeric HFB II comprising an N-terminal sequence from SC3, the expression product was compared to native HFBII with respect to surface modulating properties. The chimeric molecule showed a stronger decrease of the water contact angle after bringing the respective hydrophobin solution into contact with a specimen than the native class II hydrophobin. Furthermore, it also increased the stability of the surface coating, thus rendering the coating of Teflon® more resistant to washing with detergents, as compared to coating with native HFB II. It was therefore surprisingly found that the coating properties of class II hydrophobin HFBII were improved with respect to the change of the water contact angle and the resistance to washing with SDS.

A potential use of the chimeric surface active proteins of the invention is therefore the modification of surfaces by coating leading to e.g. increased wettability of these surfaces, such as for example Teflon®.

Another potential application is the use of the chimeric surface active proteins as galenic excipients, e.g. to achieve prolonged stability of tablets in acidic milieu as compared to a non surface active protein (bovine serum albumin) as control or as compared to, for example, a native surface active protein such as a native class II hydrophobin.

As is shown in the examples, the coating of tablets with a biopolymer consisting of alginate with an admixture of hydrophobin yielded beneficial properties regarding sustained release of a pharmaceutical composition. Coating with the chimeric hydrophobin resulted in prolonged stability of the tablets as compared to coating with native class II hydrophobin.

The present invention thus provides a means for modulating the properties of naturally occurring surface active proteins with respect to the feasibility of recombinant expression and surface modification characteristics.

Further potential applications of the chimeric surface active proteins of the present invention are their use as stabilizers in emulsions and foams, for increasing the wettability of hydrophobic surfaces as well as their use as excipients in galenic and pharmaceutical or cosmetic compositions.

In a preferred embodiment of the nucleic acid molecule of the invention, the first surface active protein and the second surface active protein are each independently selected from the group consisting of hydrophobins, latherins, chaplins, clathrins, alasan, sapB, curlins, rodlins and surf actins.

These surface active proteins are well known to the skilled person and are defined in accordance with the common general knowledge of the skilled person and the prior art, such as for example the prior art recited herein above.

In a more preferred embodiment, the first surface active protein and the second surface active protein are hydrophobins.

The term "chimeric hydrophobin" is used herein for a chimeric surface active protein of the invention wherein the first surface active protein and the second surface active protein are hydrophobins.

Hydrophobins are small cysteine-rich fungal surface active proteins of about 10 kDa in size, which self-assemble at hydrophilic-hydrophobic surfaces or interfaces into highly ordered amphipathic layers. They are characteristic of filamentous fungi, for example of *Schizophyllum commune* or *Trichoderma reesei* and are found as structural proteins on surfaces of aerial structures of fungi where the hydrophobic coating is proposed to have a protecting role both against desiccation, wetting and protecting the conidia of filamentous fungi against extreme environmental conditions, e.g. acidic pH or thermal stress (Ying, S. H. and Feng, M. G., Relationship between thermo-tolerance and hydrophobin-like proteins in aerial conidia of *Beauveria bassiana* and *Paecilomyces fumosoroseus* as fungal bio-control agents. J Appl Microbiol. 2004; 97(2):323-31). It was also suggested that hydrophobins could mediate the attachment of fungal structures to their targets by modifying host surfaces (Linder, M. B., et al., Hydrophobins: the protein-amphiphiles of filamentous fungi, FEMS Microbiol. Rev. 29, 2005, 877-896).

Two classes of hydrophobins can be distinguished based on aqueous solubility and hydropathy. Class I hydrophobins form highly insoluble aggregates which can only be dissolved with strong acids such as TFA. Class II hydrophobins are more readily solubilized and can be dissolved in aqueous solutions of organic solvents. Database searches of hydrophobin gene sequences showed that class II hydrophobins have been observed thus far only in ascomycota, whereas class I hydrophobins occur both in basidiomycota and ascomycota. However, the biological significance of the existence of these two classes remains unclear. Because of the low sequence similarity between class I and class II hydrophobins it is speculated that class II hydrophobins have evolved independently of the class I hydrophobins and thus represent a case of convergent evolution. Besides the highly conserved eight cysteine residues, the hydrophobins share only a few conserved residues, leaving space for numerous variants with specific properties.

The most thoroughly characterized class I hydrophobin is SC3 of *Schizophyllum commune* (Schuren, F. H. and Wessels, J. G., Gene 1990, 90 (2): 199-205), although other members of this class have similar properties. Upon contact with hydrophilic-hydrophobic interfaces, SC3 monomers self-assemble into a 10 nm thick amphipathic film. The hydrophilic and hydrophobic sides of the SC3 membrane are moderately hydrophilic (comparable to carbohydrate) and highly hydrophobic (comparable to Teflon®), respectively.

A representative class II hydrophobin is HFBII from *Trichoderma reesei* (Nakari-Setälä T, et al., Differential expression of the vegetative and spore-bound hydrophobins of *Trichoderma reesei*-cloning and characterization of the hfb2 gene. Eur J Biochem. (1997), 248(2):415-23), which is also being used for coating surfaces (Lumsdon, S. O., et al., Adsorption of hydrophobin proteins at hydrophobic and hydrophilic interfaces. Colloids Surf B Biointerfaces (2005), 44(4): 172-178). HFBII has been described to be very soluble in water and to form multimers in solution and in surface films (Szilvay, G. R. et al., Behavior of *Trichoderma reesei* hydrophobins in solution: Interactions, dynamica, and multimer formation, Biochemistry 2006, 45: 8590-8598). It can be utilized to confer foam stability to aerated food products (US 2006/0024417 A1) and to inhibit growth of ice crystals in frozen products (US 2006/0024419 A1).

In accordance with the present invention, the term "hydrophobins" refers to proteins of the general structural formula (I)

$$X_n\text{-}C^1\text{-}X_{1\text{-}50}\text{-}C^2\text{-}X_{0\text{-}5}\text{-}C^3\text{-}X_{1\text{-}100}\text{-}C^4\text{-}X_{1\text{-}100}\text{-}C^5\text{-}X_{1\text{-}50}\text{-}C^6\text{-}X_{0\text{-}5}\text{-}C^7\text{-}X_{1\text{-}50}\text{-}C^8\text{-}X_m \qquad (I),$$

wherein X can be the same or is different and is independently selected from any one of the naturally occurring amino acids (Phe, Leu, Ser, Tyr, Cys, Trp, Pro, His, Gln, Arg, Ile, Met, Thr, Asn, Lys, Val, Ala, Asp, Glu, Gly). The indices adjacent to X in each case indicate the number of amino acids, wherein n and m independently of each other represent natural numbers from 0 to 500, preferably from 15 to 300.

C represents cysteine, alanine, serine, glycine, methionine or threonine, wherein at least four of the amino acids designated by $C(C^1-C^8)$ in formula (I) are cysteine. More preferably at least 5, such as at least 6 and more preferably at least 7 of the positions $C^1$ to $C^8$ are cysteines. The cysteines may either be present in reduced form or can form disulfide bridges with each other. Preferably, the cysteines form at least 1, more preferably at least 2, even more preferably 3 and most preferably 4 intra-molecular disulfide bridges. In the case where not all C are cysteines but amino acids of similar sterical structure such as alanine, serine, glycine, methionine or threonine, it is preferred that they replace cysteines in pairs that would normally be capable of forming intra-molecular disulfide bridges with each other.

It will be understood by the skilled person that when cysteines, serines, alanines, glycines, methionines or threonines are additionally present in the positions indicated by X, the numbering of the individual C positions in the general formulae can change accordingly. The proteins used in accordance with the invention can, in addition, be modified in their polypeptide sequence by, for example, glycosylation, acetylation or by chemical crosslinking, such as for example with glutaraldehyde.

Hydrophobins of the above formula and the preparation thereof are known in the art, such as for example in WO 2006/103230 recited above.

Especially preferred in the context of the present invention is a chimeric surface active protein comprising sequences derived from fungal hydrophobins.

In a further preferred embodiment, the first surface active protein is a class I hydrophobin and/or the second surface active protein is a class II hydrophobin.

Based on differences in hydropathy patterns and biophysical properties (e.g. solubility, surface layer formation and stability), hydrophobins are divided into two classes, namely class I hydrophobins and class II hydrophobins (Hakanpää et al., The Journal of Biological Chemistry 2004; 279:534-539). Thus, the members of the class I hydrophobins and class II hydrophobins, each share common properties which allow for the separation into the two classes; cf. FIG. 5. Due to the common hydropathy patterns and biophysical properties of class I hydrophobins and class II hydrophobins, respectively, in accordance with the invention, a class I hydrophobin can be exchanged by a different class I hydrophobin on the one hand, and a class II hydrophobin can be exchanged by a different class II hydrophobin on the other hand.

In accordance with the present invention, the class I hydrophobin can thus be any class I hydrophobin, such as for example TT1 from *Talaromyces thermophilus* (Stolk, A. C. and Samson, R. A., Stud. Mycol. 2: 53)), POH1, -2, -3 from *Pleurotus ostreatus* (Asgeirsdottir, S. A. et al., Microbiol. 1998, 144: 2961-2969), EAS from *Neurospora crassa* (Lauter, F. R. et al., Genes Dev. 1992, 6: 2373-2381) and others. Similarly, the class II hydrophobin can be any one selected from the group of class II hydrophobins, such as for example HFB I and II from *Trichoderma reesei* (Nakari-Setälä T, et al., Differential expression of the vegetative and spore-bound hydrophobins of *Trichoderma reesei*-cloning and characterization of the hfb2 gene. Eur J Biochem. (1997), 248(2):415-23) or Hcf-5 and Hcf-6 from *Cladosporium fulvum*. Recombinant expression of hydrophobin fusion proteins in *E. coli* comprising class I hydrophobins have been disclosed in the art, for example, in WO 2006/082251. However, up to the present invention the combination of class I and class II hydrophobins resulting in a new functional molecule with improved properties has not been described.

In a more preferred embodiment, the class I hydrophobin is SC3 from *Schizophyllum commune* (Schuren, F. H. and Wessels, J. G., Two genes specifically expressed in fruiting dikaryons of *Schizophyllum commune*: homologies with a gene not regulated by mating-type genes, Gene 90 (2), 199-205 (1990)) and the class II hydrophobin is HFBII from *Trichoderma reesei* (Nakari-Setala, T., Aro, N., Ilmen, M., Munoz, G., Kalkkinen, N. and Penttila, M. Differential expression of the vegetative and spore-bound hydrophobins of *Trichoderma reesei*-cloning and characterization of the hfb2 gene, Eur. J. Biochem. 248 (2), 415-423 (1997)).

In a further more preferred embodiment, the nucleic acid molecule of the invention comprises: (a) a nucleic acid molecule encoding a polypeptide having the amino acid sequence of SEQ ID NO:2; (b) a nucleic acid molecule having the nucleic acid sequence of SEQ ID NO:1; (c) a nucleic acid molecule having the sequence of SEQ ID NO:1, wherein each thymidine is replaced by uridine; (d) a nucleic acid molecule that is degenerate with respect to the nucleic acid molecule of (b) or (c); or (e) a nucleic acid molecule of any of (a) to (d), wherein the nucleic acid molecule is devoid of between 0 and 10 of the most N-terminal amino acids and/or the most C-terminal amino acids thereof.

In this regard, it is preferred with increasing preference that the N-terminal portion and/or the C-terminal portion is devoid of between 0 and 9, between 0 and 8, between 0 and 7, between 0 and 6, between 0 and 5, between 0 and 4, between 0 and 3, between 0 and 2, or 0 and/or 1 of the most N-terminal or the most C-terminal amino acids, respectively.

The amino acid sequence of SEQ ID NO:2 represents a preferred chimeric surface active protein which consists of an N-terminal portion that consists of the 33 amino acids starting from and including the N-terminus (the most N-terminal amino acid) of SC3 from *Schizophyllum commune* and a C-terminal portion that consists of the 69 amino acids starting form and including the C-terminus (the most C-terminal amino acid) of HFBII from *Trichoderma reesei*.

In a even more preferred embodiment, the nucleic acid molecule of the invention further encodes at least one amino acid which is heterologous to the polypeptide having the amino acid sequence of SEQ ID NO: 2 and which is located N-terminally of the polypeptide encoded by the nucleic acid molecule of the invention.

In another even more preferred embodiment thereof, the at least one heterologous amino acid comprises or is a tag, preferably a His-tag or GST-tag.

It is most preferred that the tag is a His-tag (e.g. a 6×His-tag).

In a further even more preferred embodiment, the at least one heterologous amino acid further comprises the amino acid sequence of an enzymatic cleavage site.

In this regard, it is preferred that the enzymatic cleavage site is a thrombin site.

In a most preferred embodiment, the nucleic acid molecule of the invention comprises: (a) a nucleic acid molecule encoding a polypeptide having the amino acid sequence of SEQ ID NO:4; (b) a nucleic acid molecule having the nucleic acid sequence of SEQ ID NO:3; (c) a nucleic acid molecule having the sequence of SEQ ID NO:3, wherein each thymidine is replaced by uridine; (d) a nucleic acid molecule that is degenerate with respect to the nucleic acid molecule of (b) or (c) or (e) a nucleic acid molecule of any of (a) to (d), wherein the nucleic acid molecule is devoid of between 0 and 10 of the most N-terminal amino acids and/or the most C-terminal amino acids thereof.

In this regard, it is preferred with increasing preference that the N-terminal portion and/or the C-terminal portion is devoid of between 0 and 9, between 0 and 8, between 0 and 7, between 0 and 6, between 0 and 5, between 0 and 4, between 0 and 3, between 0 and 2, or 0 and/or 1 of the most N-terminal or the most C-terminal amino acids, respectively.

The amino acid sequence of SEQ ID NO:4 represents the amino acid sequence of SEQ ID NO:2 and in addition N-terminally thereof first the amino acids representing a thrombin site, and second the amino acids representing a 6×His-tag (see FIG. 1B).

When used in accordance with the present invention the term "degenerate" means that due to the redundancy of the genetic code different nucleotide sequences code for the same amino acid.

The present invention further relates to a vector comprising the nucleic acid molecule of the invention.

Preferably, the vector is a plasmid, cosmid, virus, bacteriophage or another vector used e.g. conventionally in genetic engineering. The nucleic acid molecule of the invention may be inserted into several commercially available vectors. Non-limiting examples include prokaryotic plasmid vectors, such as of the pUC-series, pBluescript (Stratagene), the pET-series of expression vectors (Novagen), in particular pET15b, or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pClNeo (Promega). Examples for plasmid vectors suitable for *Pichia pastoris* comprise e.g. the plasmids pAO815, pPIC9K and pPIC3.5K (all from Invitrogen).

The nucleic acid molecule of the invention may be inserted into vectors such that a translational fusion with another polynucleotide is generated. The other polynucleotide may encode a protein which may e.g. increase the solubility and/or facilitate the purification of the chimeric surface active protein of the invention. Non-limiting examples include pET32, pET41, pET43. The vectors may also contain an additional expressible polynucleotide coding for one or more chaperones to facilitate correct protein folding. For vector modification techniques, see Sambrook and Russel (2001), Cold Spring Harbor Laboratory; 3rd edition. Generally, vectors can contain one or more origin of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources or produced semi-synthetically, i.e. by combining chemical synthesis and recombinant techniques. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of transcription (e.g., translation initiation codon, promoters, such as naturally-associated or heterologous promoters and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid molecule encoding the chimeric surface active protein of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed protein to a cellular compartment may be added to the coding sequence of the nucleic acid molecule of the invention. Such leader sequences are well known in the art.

Possible examples for regulatory elements ensuring the initiation of transcription comprise the cytomegalovirus (CMV) promoter, SV40-promoter, RSV-promoter (Rous sarcome virus), the lacZ promoter, the gai10 promoter, human elongation factor 1α-promoter, CMV enhancer, CaM-kinase promoter, the *Autographa californica* multiple nuclear polyhedrosis virus (AcMNPV) polyhedral promoter or the SV40-enhancer. For the expression in prokaryotes, a multitude of promoters including, for example, the tac-lac-promoter, the lacUV5 or the trp promoter, has been described. Examples for further regulatory elements in prokaryotes and eukaryotic cells comprise transcription termination signals, such as SV40-poly-A site or the tk-poly-A site or the SV40, lacZ and AcMNPV polyhedral polyadenylation signals, downstream of the polynucleotide. The person skilled in the art will know how to select the appropriate regulatory elements depending on the host used for expression.

Furthermore, it is preferred that the vector of the invention comprises a selectable marker. Examples of selectable markers include neomycin, ampicillin, hygromycine and kanamycin resistance and the like. Specifically-designed vectors allow the shuttling of DNA between different hosts, such as bacteria-fungal cells or bacteria-animal cells (e.g. system available at Invitrogen).

An expression vector according to this invention is capable of directing the replication, and the expression, of the nucleic acid molecule and encoded chimeric surface active protein of the invention.

Suitable expression vectors which comprise the described regulatory elements are known in the art such as Okayama-Berg cDNA expression vector pcDV1 (Pharmacia), pRc/CMV, pcDNA1, pcDNA3 (Invitrogene, as used, inter alia in the appended examples), pSPORT1 (GIBCO BRL) or pGEMHE (Promega), or prokaryotic expression vectors, such as lambda gt11, pJOE, the pBBR1-MCS-series, pJB861, pBSMuL, pBC2, pUCPKS, pTACT1 or, preferably, the pET vector (Novagen).

The nucleic acid molecule of the invention as described herein above may be designed for direct introduction or for introduction via liposomes or vectors such as phage vectors or viral vectors (e.g. adenoviral, retroviral) into the cell. Additionally, baculoviral systems or systems based on vaccinia virus or Semliki Forest virus can be used as eukaryotic expression systems for the nucleic acid molecule of the invention.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the nucleic acid molecule of the invention may be ligated between e.g. the PelB leader signal, which directs the recombinant protein in the periplasm and the gene III in a phagemid called pHEN4 (described in Ghahroudi et al, 1997, FEBS Letters 414:521-526). Additional optional elements include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Alternatively, the recombinant polypeptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid molecule can also be amplified to express large amounts of the encoded polypeptide. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present invention further relates to a non-human host transformed with the vector of the invention. Preferably, the host is a cell, such as a unicellular organism or an isolated cell, which may be part of a cell culture. The cell may be a primary cell or part of a cell line (either a primary or an established cell line). The host from which the host cell is derived may be any prokaryote or eukaryotic cell.

The "host" in accordance with the invention may be produced by introducing the nucleic acid molecule or vector(s) of the invention into the host which upon its/their presence mediates the expression of the nucleic acid molecule of the invention encoding the chimeric surface active protein of the invention.

Suitable prokaryotes (bacteria) useful as hosts for the invention are those generally used for cloning and/or expression like *E. coli* (e.g., *E coli* strains BL21, HB101, DH5a, XL1 Blue, Y1090 and JM101), *Salmonella* spec. (e.g. *typhimurium*), *Serratia* spec. (e.g *marcescens*), *Burkholderia glumae, Pseudomonas* spec. (e.g. *putida, fluorescens, stutzeri*), *Streptomyces* spec. (e.g. *lividans, albus, coelicolor*), *Lactococcus lactis, Mycobacterium smegmatis, Corynebacterium* spec. (*glutamicum*), *Lactobacillus* spec., *Bacillus* spec. (*subtilis, megaterium*).

A suitable eukaryotic host cell may e.g. be a vertebrate cell, an amphibian cell, a fish cell, an insect cell, a fungal/yeast cell, a nematode cell or a plant cell. The insect cell may e.g. be a *Spodoptera frugiperda* cell, a *Drosophila* S2 cell or a *Spodoptera* Sf9 cell, the fungal/yeast cell may e.g. be a *Saccharomyces cerevisiae* cell, *Pichia pastoris* cell or an *Aspergillus* cell, the plant cell may e.g. be from *Oryza, Pisum,* or *Zea*. It is preferred that the vertebrate cell is a mammalian cell.

Mammalian host cells that could be used include, human Hela, 293, H9, Bowes melanoma and Jurkat cells, mouse NIH3T3 and C127 cells, Cos 1, Cos 7 and CV1, quail QC1-3 cells, mouse L cells and Chinese hamster ovary (CHO) cells. Alternatively, the chimeric surface active protein can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded chimeric surface active protein. The DHFR (dihydrofolate reductase) marker is useful to develop cell lines that carry several hundred or even several thousand copies of the gene of interest. Another useful selection marker is the enzyme glutamine synthase (GS) (Murphy et al. 1991, *Biochem J.* 227:277-279; Bebbington et al. 1992, *Bio/Technology* 10:169-175). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

Preferred examples for hosts to be genetically engineered with the nucleic acid molecule or the vector(s) of the invention is *E. coli*, a yeast cell and/or a species of the genus *Bacillus* (e.g. *B. subtilis*). Most preferably, the host is *E. coli*.

Appropriate culture media and conditions for the above-described hosts are known in the art. The present invention further relates to a method for the production of a chimeric protein having the biochemical activity of a surface active protein comprising culturing the host of the invention under suitable conditions and isolating the recombinant chimeric surface active protein produced.

The term "culturing" as used herein specifies the process by which the host is grown under controlled conditions. These conditions may vary dependent on the host used. Suitable conditions for culturing a prokaryotic or eukaryotic host are well known to the person skilled in the art.

For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depending on the molecule to be over-expressed. In general, the skilled person is also aware that these conditions may have to be adapted to the needs of the host and the requirements of the protein expressed. In case an inducible promoter controls the nucleic acid molecule of the invention in the vector present in the host cell, expression of the protein can be induced by addition of an appropriate inducing agent. Suitable expression protocols and strategies are known to the skilled person.

Depending on the cell type and its specific requirements, mammalian cell cultures can e.g. be carried out in RPMI or DMEM medium containing 10% (v/v) FCS, 2 mM L-glutamine and 100 U/ml penicillin/streptomycin. The cells can be kept at 37° C. in a 5% $CO_2$, water saturated atmosphere.

Suitable media for insect cell culture is e.g. TNM+10% FCS or SF900 medium. Insect cells are usually grown at 27° C. as adhesion or suspension culture.

The various steps in the isolation method may include freeing the protein from a matrix that confines it, separating the proteinaceous and non-proteinaceous parts of the mixture, and finally separating the chimeric surface active protein from all other proteins. Isolation steps exploit differences in protein size, physico-chemical properties and binding affinity. In this regard it is preferred that the protein is exported to the culture medium. Depending on the vector construction employed, the protein may be exported to the culture medium or maintained within the host cell. Methods of isolating the polypeptide produced are well-known in the art and comprise, without being limiting, method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001, loc. cit.

In accordance with this embodiment, a method is provided that allows for the production of the chimeric surface active protein of the invention by gene expression of the nucleic acid molecule of the invention in a suitable host. The gene expression can be carried out either in a heterologous or in a homologous host strain. Such methods are well known to the person skilled in the art. The various steps in the process of expressing the chimeric surface active protein of the invention may be modulated, such as for example the transcription, RNA splicing, translation, and post-translational modification of the chimeric surface active protein of the invention by methods know in the art. Accordingly, such modulation may allow for control of the timing, location, and amount of chimeric surface active protein produced.

The present invention further relates to a chimeric protein having the biochemical activity of a surface active protein encoded by the nucleic acid molecule of the invention and/or produced by the method of the invention.

The chimeric surface active protein of the invention may be generated by molecular cloning techniques. Recombinant expression can be accomplished using expression vectors and hosts as described above.

Furthermore, the surface active proteins that can be used as a source in the generation of the chimeric proteins of the invention can also be isolated from natural sources. The isolation of hydrophobins, for example, has been described e.g. in Wósten et. al., Eur. J. Cell Biol. 63, 122-129 (1994) or in WO 96/41882. Also the synthesis of hydrophobins that do not occur naturally by means of chemical and/or biotechnological methods of preparation has been described in the art, e.g. in Scholtmeijer, K. et al. (Surface modifications created by using engineered hydrophobins, Appl. Environ. Microbiol. 2002, 68(3): 1367-73), in the patent application WO 2006/082251A2 as well as in the patent application WO 2006/082253A2.

In addition, the chimeric protein of the invention may further be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154).

Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. Chemical synthesis also includes the solid phase procedure described by Houghton (Proc. Natl. Acad. Sci., 1985, 82: 5131). Furthermore, the chimeric surface active protein of the invention may be produced semi-synthetically, for example by a combination of recombinant and synthetic production.

The present invention also relates to a composition comprising the chimeric protein of the invention.

The term "composition", as used in accordance with the present invention, relates to a composition which comprises at least one chimeric surface active protein of the invention. It may, optionally, comprise furthermore excipients, additives and/or adjuvants. Examples of additional components include surfactants, such as for example anionic, non-ionic, amphoteric and/or cationic surfactants. The composition may optionally comprise further molecules capable of altering the characteristics of the chimeric surface active protein of the invention thereby, for example, reducing, stabilizing, delaying, modulating and/or activating their function. Furthermore, the composition may comprise a plurality of different chimeric surface active proteins. The composition may be in solid, liquid or gaseous form and may be, inter alia, in the form of (a) powder(s), (a) tablet(s), (a) solution(s) or (an) aerosol(s).

In a preferred embodiment, the composition is a pharmaceutical composition.

In accordance with the present invention, the term "pharmaceutical composition" relates to a composition for administration to a patient, preferably a human patient. The pharmaceutical composition of the invention comprises the compounds, i.e. chimeric surface active protein(s), as recited above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include sodium chloride solutions, phosphate buffered sodium chloride solutions, water, emulsions, such as oil/water emulsions, various types of wetting agents, sterile solutions, organic solvents including DMSO etc. Preferably the carrier is a carrier suitable for topical administration. The carrier suitably contains minor amounts of additives such as substances that enhance chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

Compositions comprising such carriers can be formulated by well known conventional methods. Generally, the formulations are prepared by contacting the components of the pharmaceutical composition uniformly and intimately with liquid carriers or finely divided solid carriers or both. Then, if necessary, the product is shaped into the desired formulation.

These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. Generally, the regimen as a regular administration of the pharmaceutical composition should be in the range of 0.001 to 5% per weight and day. However, a more preferred dosage might be in the range of 0.01 mg to 100 mg, even more preferably 0.01 mg to 50 mg and most preferably 0.01 mg to 10 mg per application. Preferably, one application is administered per day, although the invention also envisages several applications per day. Administration of pharmaceutical compositions of the invention may be effected by different ways, e.g., by intravenous, intraperitoneal, subcutaneous, intramuscular, topical, intradermal, intranasal or intrabronchial administration. Most preferably, the administration is a topical administration.

The term "topical" as used herein refers to modes of administration which include applications to body surfaces, such as the skin, hair, teeth or keratinaceous surfaces such as finger- and toenails as well as animal hoofs or tortoiseshell. Typically, topical formulations are administered in the form of a cream, gel or lotion or as transdermal patches.

The components of the pharmaceutical composition to be used for therapeutic administration must be sterile. Sterility is readily accomplished by filtration through sterile filtration membranes (e.g., 0.2 micron membranes).

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The solution is preferably prepared by reconstituting the lyophilized compound(s) using bacteriostatic water-for-injection.

Preservatives and other additives may also be present such as, for example, antimicrobials, anti-oxidants, chelating agents, inert gases and the like. Furthermore, the pharmaceutical composition may comprise further agents depending on the intended use of the pharmaceutical composition.

The pharmaceutical composition comprising the chimeric surface active protein of the invention may be particularly useful for improving the local and systemic availability of drugs for the treatment of diseases, preferably, diseases selected from bacterial or viral infections (non-limiting examples include tuberculosis, syphilis, herpes simplex, herpes zoster, verrucae), fungal infections (including, without being limiting, dermatomycosis, onychomycosis, candidosis like thrush), tumor and autoimmune diseases amenable to topical treatment (including, without being limiting, melanoma, kaposi sarcome, lupus erythemathosis). Additionally, the use in the treatment of skin irritations (e.g. sun burn), skin diseases (non-limiting examples include psoriasis, dermatitis, urticaria, acne) and infestations by parasites (e.g. ticks, mites) are envisaged. One example for a potential use of hydrophobins including chimeric hydrophobins as permeation enhancers for transungual delivery of the drug terbinafine in the treatment of onchomycosis is described in Vejnovic, I. et al. (Permeation studies of novel terbinafine formulations containing hydrophobins through human nails in vitro, *Int J Pharm* 2010 Sep. 15; 397(1-2):67-76).

In another preferred embodiment, the composition is a cosmetic composition.

In accordance with the present invention, the "cosmetic composition" comprises the compounds, i.e. chimeric surface active protein(s), as recited above. The cosmetic composition of the present invention may, optionally and additionally, comprise a carrier, i.e. a non-toxic solid, semisolid or liquid filler, diluent, encapsulating material or formulation auxiliary of any type, as defined above for the pharmaceutical composition. The cosmetic composition can be, for example, in the form of a creamy composition, an aqueous solution, an emulsion or a gel. Uses of the cosmetic composition of the invention include, without being limiting, skin protection or the preparation of shampoos and conditioners.

The present invention further relates to a method of coating and/or impregnating a material, comprising contacting the material with the chimeric protein of the invention or the composition of the invention.

The term "coating a material" in accordance with the invention refers to the incubation a said material with the chimeric surface active protein of the invention or the application of a layer comprising the chimeric surface active protein of the invention or the composition of the invention onto a material. In other words, the surface of the material is covered, preferably totally covered, with the chimeric surface active protein or the composition of the invention. Non-limiting examples include the spraying of a material with the chimeric surface active protein or the composition of the invention or immersing the material therein.

In accordance with the present invention, the term "impregnating a material" refers to the mixing or incubation of a material and/or the saturation of the material with the chimeric surface active protein or the composition of the invention. Non-limiting examples include the impregnation of a medical bandage with the chimeric surface active protein or the composition of the invention or the incorporation of the chimeric surface active protein or the composition of the invention into a matrix.

The temperature at which treatment is performed is generally ambient temperature, i.e. room temperature of about 25° C. However, higher or lower temperatures within a range of between 4° C. and 50° C. are also applicable depending on the temperature tolerance of the object to be treated. The duration of treatment is determined by the person skilled in the art and can be from a few seconds up to several hours. After treatment, the surface can be rinsed, for example with water, to remove excess treatment solution.

In a preferred embodiment of the method of the invention, the material is tablets.

As shown in the appended examples, the coating of tablets with a biopolymer consisting of alginate with an admixture of hydrophobin yielded beneficial properties regarding sustained release of a pharmaceutical composition. Coating with the chimeric hydrophobin was found to confer enhanced stability of said tablets to an acidic aqueous milieu as compared to the class II hydrophobin making up the major part of the chimeric protein.

The use of the chimeric surface active proteins as galenic excipients is therefore an advantageous use of the method of the invention, e.g. to achieve prolonged stability of tablets in acidic milieu as compared to a non surface active protein (bovine serum albumin) or as compared to, for example, a native class II hydrophobin.

In another preferred embodiment of the method of the present invention, the material is selected from the group consisting of polytetrafluorethylen, thermoplastic polyolefins, silicon, metal, glass, wood or other material of biological origin, plastic and lacquered surfaces.

All of the materials described herein are well known to the skilled person and are defined in accordance with the prior art and the common general knowledge of the skilled person.

The term "polytetrafluorethylen" as used herein refers to a synthetic fluoropolymer of tetrafluoroethylene, which is best known by the DuPont brand name Teflon®.

"Thermoplastic polyolefins", in accordance with the present invention, refer to thermoplastic elastomers on the basis of olefins, which are generally defined as low modular elastic materials that can be extended to at least twice their original size at ambient temperature and return to their original size when released.

The term "other material of biological origin" comprises both naturally occurring materials as well as naturally occurring materials that have been further processed. Non-limiting examples of naturally occurring materials and those, which have been further processed include cotton, wood, cellulosic materials and the like.

The term "material" in this context also refers to cells, such as for example skin cells or keratinocytes. It is envisaged that said cells may either be part of a tissue, or alternatively cells which are cultured, for example in a three dimensional (e.g. a suspension culture) or monolayer culture. Thus, the surface of this material may be, in the first case, the surface of the tissue and in the second case the surface of the individual cells.

The term "plastic" or "plastics", in accordance with the present invention, refers synthetic or semisynthetic organic amorphous solid materials used in the manufacture of industrial products. Plastics are typically polymers of high molecular mass, examples are polyethylene, polystyrene, polyvinyl chloride and polytetrafluoroethylene (PTFE)

The term "lacquered surfaces", as used herein, refers to surfaces that have been coated with enamel varnish, paint or laquer. Lacquer refers to polymers such as nitrocellulose and acrylic compounds (e.g. acrylic resin, polyurethane), dissolved in volatile organic compounds, e.g. butyl acetate and xylene or toluene.

As mentioned above, the present invention provides chimeric surface active proteins for the coating of materials and/or surfaces and the impregnation of materials. As shown in the examples below, a chimeric hydrophobin was surprisingly found to change the water contact angle on the surface of coated objects. In particular, the wettability of Teflon® was shown to be increased by coating with the chimeric hydrophobin of the invention as compared to coating with a class II hydrophobin.

When the composition of the invention is used for coating/impregnating, the composition preferably comprises at least one chimeric surface active protein and an aqueous solvent, for example a solvent of which at least 50% by weight is water. For example, aqueous solutions may be used which have been obtained in the synthesis, isolation and/or purification of the chimeric surface active proteins. Depending on purity, those solutions may still contain residues of materials from the synthesis. It will be understood, however, that it is also possible for the chimeric surface active protein to be isolated in solvent-free form, for example by freeze-drying, and to be formulated into a composition in a second step.

In order to prepare a coating/impregnating solution the chimeric surface active protein of the invention is preferably used in a form free of organic solvents, i.e. in the form of formulations based on water or any other pharmaceutically acceptable solubility agent. It will be understood that mixtures of solvents can also be used. The nature of the solvent depends, for example, on the chimeric surface active protein, the nature of the surface/material to be treated and its use and can be chosen by the skilled person based in the information available in the art and his/her common general knowledge.

The amount of the chimeric surface active proteins for use in the method of the invention can be determined by the person skilled in the art in accordance with the nature of the surface/material and/or the intended use. Suitable amounts of chimeric surface active protein for use in a pharmaceutical composition are defined above. As a further non-limiting example an amount of 0.01 to 10.0 mg/ml might be used for achieving a change in the properties of a surface/material. More preferably, a range from 0.1 to 5 mg/ml and most preferably 0.2 mg/ml may be used.

The figures show:

FIG. 1: A, construction of a chimeric surface active protein of the invention comprising an N-terminal portion of SC3 and a C-terminal portion of HFBII, which replaces the missing portion of SC3. The fusion site is located at the first cysteine of HFBII.; B, nucleic acid sequence and translation into amino acid sequence of the chimeric molecule of the invention, comprising His-tag, thrombin site, and sequences originating from hydrophobins SC3 (class I) and HFBII (class II); C, additional chimeric constructs comprising different class I and class II hydrophobins.

Figure 2A:
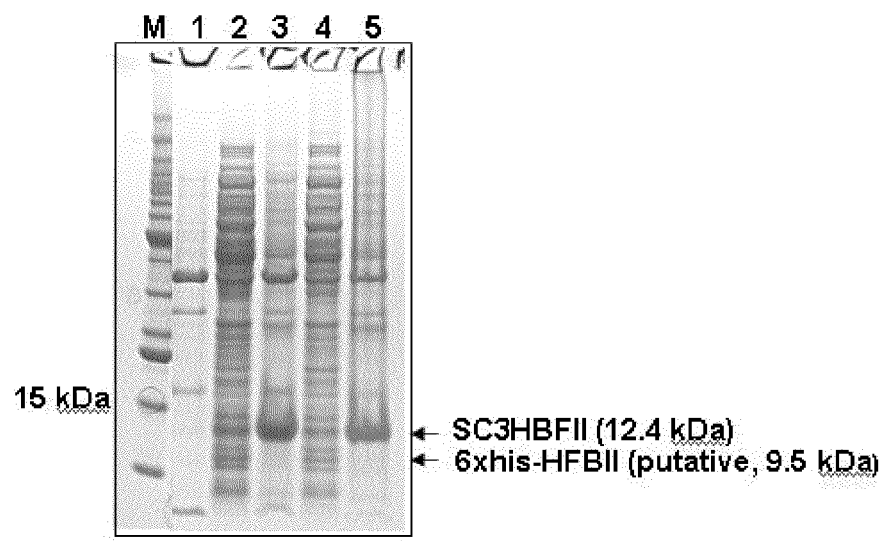
Figure 2B:
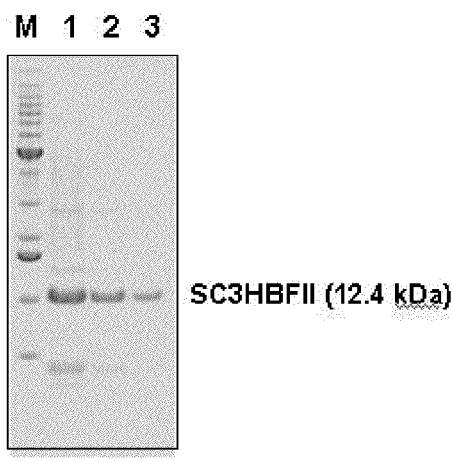
Figure 3:
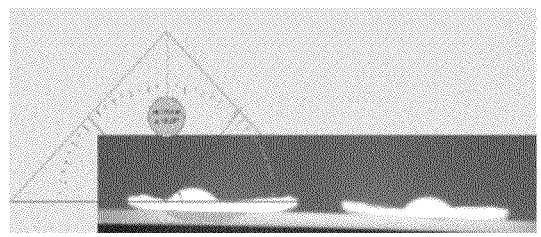
Figure 3:
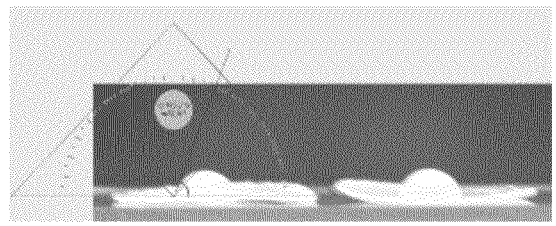
Figure 3:
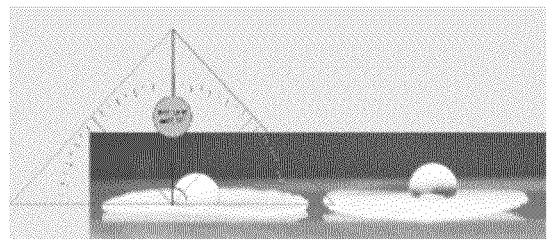

FIG. 2: Expression of HFBII (native) and SC3/HFBII (chimera), respectively, in E. coli:
A: M, molecular weight marker; 1, chimera (1.5 h of expression); 2, HFBII (7.5 h); 3, chimera (7.5 h); 4, HFBII (24 h); 5, chimera (24 h);
B: M, molecular weight marker; 1, 15 µg; 2, 7.5 µg; 3, 3.75 µg purified chimera FIG. 3: Measurement of the water contact angle (WCA) of water droplets on Teflon® plates coated with the chimeric surface active protein of the invention (chimeric hydrophobin; A) or with class II hydrophobin HFB II (B). As control, the WCA on an uncoated Teflon® plate is shown (C).

Figure 4:
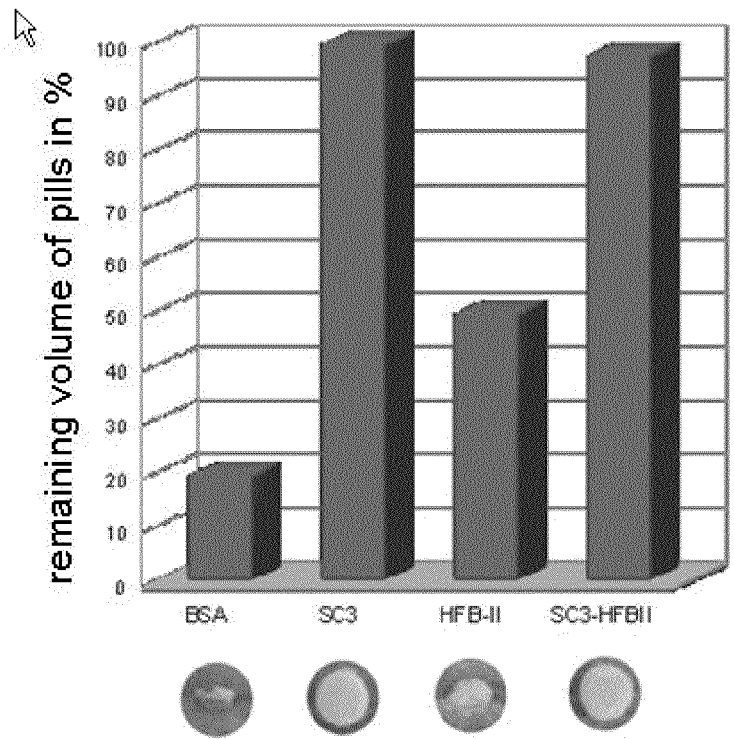

FIG. 4: Stability of alginate coated tablets in acidic aqueous milieu (pH 1.0)

Figure 5:
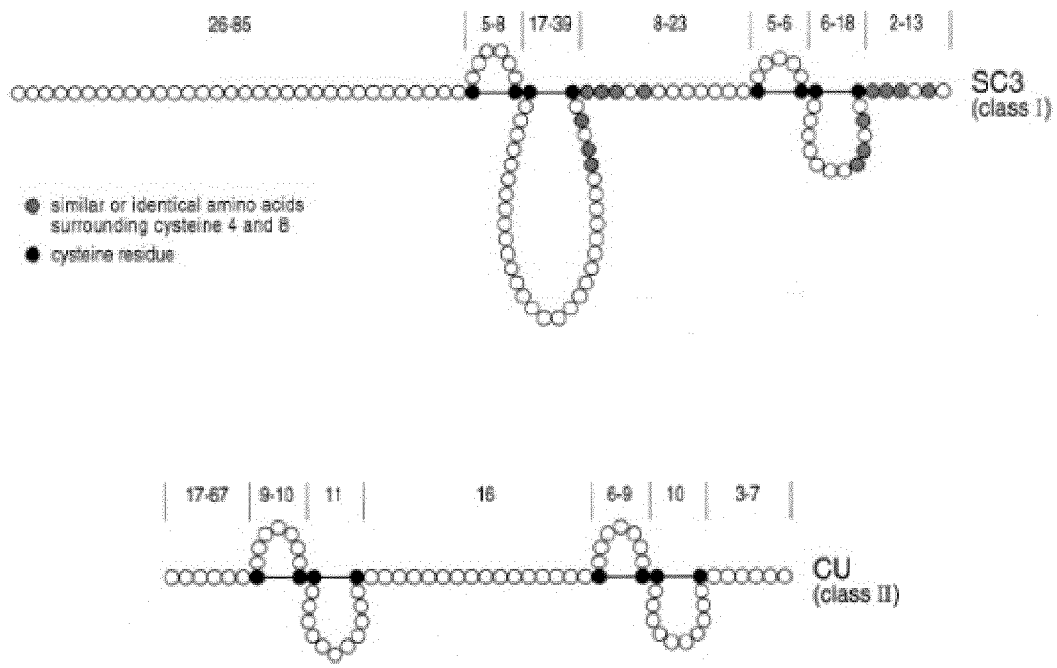

FIG. 5: Provides a schematic overview of the differences between class I and class II hydrophobins in amino acid level and the secondary protein structure (Wösten and Vocht (2000), Biochim Biophys Acta, 1469:79-86). Without wishing to be bound by theory, in particular, the size of the N-terminus and the size of the loop, which is formed via disulfide bonding between Cys3 and Cys4, differ between class I and class II hydrophobins.

The examples illustrate the invention. The broad scope of this invention is best understood with reference to the following examples, which are not intended to limit the inventions to the specific embodiments.

EXAMPLE 1

General Procedures

Preparation of Hydrophobins

A portion of class I hydrophobin from *Schizophyllum commune* (SC3) and a portion of class II hydrophobin from *Trichoderma reesei* (HFBII) were used to generate a chimeric surface active protein according to the present invention, namely a chimeric hydrophobin (SEQ ID NO:2).

The nucleic acid sequences for said hydrophobins were obtained from NCBI/Gene Bank: sc3 accession number 169868 (Schuren, F. H. and Wessels, J. G., Two genes specifically expressed in fruiting dikaryons of *Schizophyllum commune*: homologies with a gene not regulated by mating-type genes, Gene 1990, 90 (2), 199-205); hfb2 accession number Y11894 (Nakari-Setala, T., Aro, N., Ilmen, M., Munoz, G., Kalkkinen, N. and Penttila, M., Differential expression of the vegetative and spore-bound hydrophobins of *Trichoderma reesei*-cloning and characterization of the hfb2 gene, Eur. J. Biochem. 1997, 248 (2), 415-423).

After removal of the native signal sequences and optimization of codon usage towards *E. coli, B. subtilis, K. lactis, Yecorina* sp. the cDNAs were synthesized by Sloning Bio-Technology, Pucheim, Germany. Hydrophobin nucleic acid molecules were cloned into an expression vector (pET15b, Novagen) allowing the fusion of the hydrophobin sequence to a 6×his-tag sequence. The vector was then transformed into the expression host *E. coli* BL21 (FIG. 1A).

Construction of Chimeric Molecule on Nucleic Acid Level

The nucleic acid molecule (cDNA SEQ ID NO:1) encoding the chimeric surface active protein comprising the N-terminal 33 amino acids of SC3 (class I) and the 69 C-terminal amino acids of HFBII (class II) was constructed by fusing the corresponding template parts based on the cDNA sequences optimized for E. coli, B. subtilis, K. lactis, Yecorina sp. codon usage as described above.

Correct fusion was confirmed by sequencing and the cDNA cloned into a pET expression vector. Sequences were assembled in such a way that purification of the expression product was enabled by adding a tag-sequence of six histidines and a thrombin cleavage site for potential removal of the tag after purification. The assembled nucleic acid sequence is shown in FIG. 1B.

Expression

Small scale expressions of 6×his-SC3, 6×his-HFBII and chimeric hydrophobin, constructed as described above, in E. coli BL21 were performed in shaker cultures with 200 ml LB medium and a suitable antibiotic (ampicillin, 50 μg/ml). Protein expression was induced by addition of IPTG.

Attempts to express 6×his-HFBII from a pET vector in E. coli yielded no product of the expected size of 9.6 kDa (FIG. 2A, lanes 2 and 4), whereas 6×his-SC3 could be expressed without difficulties. Surprisingly, the chimeric hydrophobin consisting of a portion of the HFBII protein with the N-terminal SC3 portion yielded an expression product (FIG. 2A, lanes 3 and 5).

Fermentation of transformed E. coli BL21 with expression vector comprising 6×his-SC3 or SC3/HFBII chimeric hydrophobin cDNA, respectively, was performed in a 10 liter scale for 16 hours using ZYM-5052 medium (25 mM Na$_2$HPO$_4$, 25 mM KH$_2$PO$_4$, 50 mM NH$_4$Cl, 5 mM Na$_2$SO$_4$, 20 mM MgSO$_4$, 5 g/l glycerol, 0.5 g/l glucose, 2 g/l alpha-lactose monohydrate, 5 g/l yeast extract, and 10 g/l NZ-amines (purchased from Sigma)) in the presence of 100 μg/ml ampicillin or 25 μg/ml kanamycin, respectively. After harvest of the biomass the sedimented cells were frozen in liquid nitrogen and stored at −80° C. After treatment of thawed aliquots of sedimented cells by sonication, the released inclusion bodies were purified and solubilized by boiling the cell homogenate for 30 sec. in 1% SDS buffer and stirring for 2 h at 600 rpm at 20° C. Solutions were cleared by centrifugation and the protein-containing supernatants were passed through a 0.22 μm filter. The filtrate was subjected to affinity chromatography on nickel sepharose (GE Healthcare) and the eluted fractions were analyzed by SDS polyacrylamide gel electrophoresis. The fractions containing hydrophobin and chimeric hydrophobin protein were cumulated and these hydrophobin-containing solutions were subsequently desalted by dialysis in a Slide-A-Lyzer (Pierce) with a 10 kDa cut off membrane against water (30 ml eluate in 3 liters of water for 16 hours). The protein concentration was determined using a BCA assay (Pierce). The hydrophobin solutions were quick-frozen in liquid nitrogen and lyophilized.

6×his-SC3 was obtained in adequate amounts and was subsequently used for the coating experiments.

HFBII used herein for preparing a coating solution was obtained by fermentation of Trichoderma reesei (HFBII), since recombinant expression was not possible as described above. For coating, aqueous solutions of hydrophobins (HFBII or chimeric hydrophobin, respectively) containing 200 μg/ml protein were applied.

EXAMPLE 2

Measurement of Water Contact Angles

Teflon® specimens were coated with aqueous solutions comprising 200 μg/ml class II hydrophobin (HFBII), chimeric class I/class II hydrophobin (chimeric hydrophobin) or no hydrophobin (control) by immersion for 16 hours, subsequent washing with water, 0.1% SDS in water, and again with water. The specimen were dried at room temperature. Additional washes with 0.1% SDS in water were performed to test the stability of the hydrophobin coating towards detergent treatment. The contact angles obtained with water droplets of 5 μl after different treatment of the Teflon® plates are shown in table 1.

TABLE 1

Measurement of water contact angles on coated or uncoated Teflon ® plates

| coating | water contact angle (WCA) | | | WCA change compared to control w/o wash | | |
|---|---|---|---|---|---|---|
| | w/o wash | 1x wash | 2x wash | w/o wash | 1x wash | 2x wash |
| Chimera | 50.03 | 66.86 | 88.16 | 41.13 | 24.30 | 3.00 |
| HFB-II | 69.97 | 87.85 | 86.72 | 21.19 | 3.31 | 4.44 |
| control | 91.16 | 95.38 | 94.93 | 0 | −4.22 | −3.77 |

Results:

The data show that the chimeric surface active protein increases the wettability of the Teflon specimen as compared to the class II hydrophobin and that the coating with the chimera is considerably more stable to the first wash with detergent than the coating with the class II hydrophobin.

EXAMPLE 3

Stability of Tablets Coated with Surface Active Proteins in Aqueous Solution

Traumeel® S (Heel) tablets were coated with hydrophobin and resistance to acidic conditions of pH 1.0 was tested in a dissolution assay. Traumeel® S tablets were submersed in a solution of 2% alginate, containing 200 μg/ml SC3, chimeric hydrophobin or HFBII, respectively. As negative control a solution of alginate containing 200 μg/ml BSA and 0.002% SDS (0.002% SDS was used in all samples, experimental as well as control) was used. After short submersion of between 30 seconds to 1 minute, alginate-coated tablets were allowed to polymerize in 0.1 M CaCl$_2$ and dried over night at ambient temperature. The incubation for the dissolution test was at ambient temperature in 0.1 M HCl for 10 to 260 min.

Results:

After incubation for 260 min at a pH of 1 a prolonged integrity of the tablets coated with the alginate/hydrophobin biopolymer was clearly observed, with the class I hydrophobin SC3 and the chimeric hydrophobin being superior to the class II hydrophobin HFB II and BSA control with regard to resistance to dissolution of the coated tablet (FIG. 4).

The invention claimed is:

1. A nucleic acid molecule encoding a chimeric protein having a biochemical activity of a surface active protein, wherein said chimeric protein comprises:
(a) an N-terminal portion of a class I hydrophobin protein, including the most N-terminal amino acid of the mature class I hydrophobin protein and comprising at least the 33 N-terminal amino acids of SEQ ID NO: 2,
(b) a C-terminal portion of a class II hydrophobin protein, including the most C-terminal amino acid of the mature class II hydrophobin protein and comprising at least 20% of the mature class II hydrophobin protein starting from the most C-terminal amino acid thereof;
wherein the class I hydrophobin is SC3 from *Schizophyllum commune* and the class II hydrophobin is HFBII from *Trichoderma reesei*.

2. A nucleic acid molecule comprising:
(a) a nucleic acid molecule encoding a polypeptide comprising the amino acid sequence of SEQ ID NO:2;
(b) a nucleic acid molecule comprising the nucleic acid sequence of SEQ ID NO:1;
(c) a nucleic acid molecule having the nucleic acid sequence of SEQ ID NO:1, wherein each thymidine is replaced by uridine; or
(d) a nucleic acid molecule that is degenerate with respect to the nucleic acid molecule of (b) or (c).

3. The nucleic acid molecule of claim 2, wherein the nucleic acid molecule further encodes at least one amino acid which is heterologous to the polypeptide having the amino acid sequence of SEQ ID NO: 2.

4. The nucleic acid molecule of claim 3, wherein the at least one heterologous amino acid comprises or is a tag.

5. The nucleic acid molecule of claim 3, wherein the at least one heterologous amino acid further comprises the amino acid sequence of an enzymatic cleavage site.

6. A nucleic acid comprising:
(a) a nucleic acid molecule encoding a polypeptide having the amino acid sequence of SEQ ID NO:4;
(b) a nucleic acid molecule comprising the nucleic acid sequence of SEQ ID NO:3;
(c) a nucleic acid molecule comprising the sequence of SEQ ID NO:3, wherein each thymidine is replaced by uridine;
(d) a nucleic acid molecule that is degenerate with respect to the nucleic acid molecule of (b) or (c).

7. A vector comprising the nucleic acid molecule of any one of claims 1 and 2-6.

8. A non-human host cell transformed with the vector of claim 7.

9. A method for the production of a chimeric protein having the biochemical activity of a chimeric hydrophobin protein comprising culturing the host cell of claim 8 under suitable conditions and isolating the recombinant chimeric protein produced.

10. The nucleic acid molecule of claim 4, wherein the tag is a His-tag or a GST-tag.

11. The nucleic acid molecule of claim 1, wherein the encoded chimeric protein provides increased wettability of a Teflon™ surface to which it is applied compared to the wettability provided by native hydrophobin HFB-II applied to said Teflon™ surface.

12. The nucleic acid of claim 1, wherein the chimeric protein comprises at least 40% of the mature class II hydrophobin protein.

13. The nucleic acid of claim 1, wherein the chimeric protein comprises at least 60% of the mature class II hydrophobin protein.

14. The nucleic acid of claim 1, wherein the chimeric protein comprises at least 80% of the mature class II hydrophobin protein.

15. The nucleic acid of claim 3, in which the at least one amino acid which is heterologous to the polypeptide having the amino acid sequence of SEQ ID NO: 2 is located at the amino terminus of the chimeric protein.

* * * * *